(12) United States Patent
Oda

(10) Patent No.: US 11,954,858 B2
(45) Date of Patent: Apr. 9, 2024

(54) INFORMATION PROCESSING APPARATUS, INFORMATION PROCESSING METHOD, AND INFORMATION PROCESSING PROGRAM

(71) Applicant: FUJIFILM CORPORATION, Tokyo (JP)

(72) Inventor: Yoshinari Oda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 336 days.

(21) Appl. No.: 17/213,234

(22) Filed: Mar. 26, 2021

(65) Prior Publication Data

US 2021/0304407 A1 Sep. 30, 2021

(30) Foreign Application Priority Data

Mar. 31, 2020 (JP) .................. 2020-065267

(51) Int. Cl.
*G06T 7/00* (2017.01)
*G06T 7/521* (2017.01)
*G16H 30/40* (2018.01)

(52) U.S. Cl.
CPC ............ *G06T 7/0014* (2013.01); *G06T 7/521* (2017.01); *G16H 30/40* (2018.01);
(Continued)

(58) Field of Classification Search
CPC .................. G06T 7/0014; G06T 7/521; G06T 2207/10028; G06T 2207/10116; G06T 2207/30068; G16H 30/40
See application file for complete search history.

(56) References Cited

U.S. PATENT DOCUMENTS 10,156,728 B2 * 12/2018 Saisho ................... G09G 5/006
11,030,604 B2 * 6/2021 Kambara ............. G06Q 20/208
(Continued)

FOREIGN PATENT DOCUMENTS

JP  2012-021909 A  2/2012
JP  2014-511731 A  5/2014
(Continued)

OTHER PUBLICATIONS

English language translation of the following: Office action dated Jan. 17, 2023 from the JPO in a Japanese patent application No. 2020-065267 corresponding to the instant patent application. This office action translation is submitted now in order to supplement the understanding of the cited references which are being disclosed in the instant Information Disclosure Statement.

*Primary Examiner* — Shefali D Goradia
(74) *Attorney, Agent, or Firm* — SOLARIS Intellectual Property Group, PLLC

(57) ABSTRACT

A CPU acquires a distance image which indicates a distance to an imaging target and is captured by a TOF camera that captures the distance image using, as the imaging target, a mammography apparatus which is an abnormality determination target. In addition, the CPU acquires reference distance image as reference distance information related to a reference value of a distance between the abnormality determination target in a reference state and the TOF camera. Further, the CPU performs determination on an abnormality appearing in an outward appearance of the abnormality determination target on the basis of the distance image and the reference distance image.

19 Claims, 10 Drawing Sheets

(52) U.S. Cl.
CPC ............... *G06T 2207/10028* (2013.01); *G06T 2207/10116* (2013.01); *G06T 2207/30068* (2013.01)

(56) References Cited

U.S. PATENT DOCUMENTS

| | | | |
|---|---|---|---|
| 2012/0051613 A1* | 3/2012 | Kamiya | .................. H04N 5/32 382/128 |
| 2016/0007944 A1* | 1/2016 | O'Connor | ............ A61B 8/0825 600/431 |
| 2017/0071558 A1 | 3/2017 | Hoornaert | |
| 2021/0019880 A1* | 1/2021 | Chan | ....................... A61B 6/502 |

FOREIGN PATENT DOCUMENTS

| | | | | |
|---|---|---|---|---|
| JP | 2017-506965 A | | 3/2017 | |
| JP | 2018-102687 | * | 5/2018 | |
| JP | 2018-102687 A | | 7/2018 | |
| JP | 2018-112568 A | | 7/2018 | |
| WO | WO-2009076303 A2 | * | 6/2009 | ............. A61B 6/466 |
| WO | WO-2010102011 A1 | * | 9/2010 | ............. A61B 6/025 |
| WO | 2019/226801 A2 | | 11/2019 | |

* cited by examiner

INFORMATION PROCESSING APPARATUS, INFORMATION PROCESSING METHOD, AND INFORMATION PROCESSING PROGRAM

CROSS-REFERENCE TO RELATED APPLICATIONS

The present application claims priority under 35 U.S.C. § 119 to Japanese Patent Application No. 2020-065267, filed on Mar. 31, 2020. The above application is hereby expressly incorporated by reference, in its entirety, into the present application.

BACKGROUND

1. Technical Field

The present disclosure relates to an information processing apparatus, an information processing method, and an information processing program.

2. Description of the Related Art

A technique is known which supports the capture of a radiographic image by a radiography apparatus using a distance image showing the distance to an imaging target. For example, JP2014-511731A discloses a technique which provides a 3D free space model for moving a moving portion without collision, using a depth image captured by a time-of-flight camera.

SUMMARY

It is desirable to perform determination on an abnormality occurring in the outward appearance of a mammography apparatus as the support for the capture of the radiographic image. However, it is difficult for the technique described in JP2014-511731A to perform the determination on the abnormality.

The present disclosure has been made in view of the above-mentioned problems, and an object of the present disclosure is to provide an information processing apparatus, an information processing method, and an information processing program that can perform determination on an abnormality occurring in the outward appearance of a mammography apparatus from a distance image.

In order to achieve the above object, according to a first aspect of the present disclosure, there is provided an information processing apparatus comprising: at least one processor; and a memory that stores commands executable by the processor. The processor acquires a distance image which indicates a distance to an imaging target and is captured by a distance image capture device that captures the distance image using, as the imaging target, a mammography apparatus which is an abnormality determination target, acquires reference distance information related to a reference value of a distance between the abnormality determination target in a reference state and the distance image capture device, and performs determination on an abnormality appearing in an outward appearance of the abnormality determination target on the basis of the distance image and the reference distance information.

According to a second aspect of the present disclosure, in the information processing apparatus according to the first aspect, the processor may determine that the abnormality has occurred in a case in which an absolute value of a difference between a distance to the abnormality determination target indicated by the distance image and the reference value is greater than an abnormality determination threshold value.

According to a third aspect of the present disclosure, in the information processing apparatus according to the second aspect, in a case in which it is determined that the abnormality has occurred, the processor may determine that, as the absolute value of the difference becomes larger, a degree of the abnormality becomes larger.

According to a fourth aspect of the present disclosure, in the information processing apparatus according to the second aspect, the processor may specify an abnormal region that is greater than the abnormality determination threshold value in the distance image, and may determine that deflection has occurred as the abnormality in a case in which a width of the specified abnormal region is equal to or greater than a type determination threshold value.

According to a fifth aspect of the present disclosure, in the information processing apparatus according to the second aspect, the processor may specify an abnormal region that is greater than the abnormality determination threshold value in the distance image, and may determine that a scratch or a crack has occurred as the abnormality in a case in which a width of the specified abnormal region is less than a type determination threshold value.

According to a sixth aspect of the present disclosure, in the information processing apparatus according to the second aspect, the abnormality determination target may be at least one of a plurality of components in the mammography apparatus, and the abnormality determination threshold value may be determined for each of the plurality of components.

According to a seventh aspect of the present disclosure, in the information processing apparatus according to the first aspect, the abnormality determination target may be at least one of a plurality of components in the mammography apparatus, and the reference distance information may be determined for each of the plurality of components.

According to an eighth aspect of the present disclosure, in the information processing apparatus according to the sixth aspect, the plurality of components may be provided with marks including portions having different distances from the distance image capture device, and the processor may determine which of the plurality of components is the abnormality determination target from an image of the mark in the distance image.

According to a ninth aspect of the present disclosure, in the information processing apparatus according to the first aspect, the processor may acquire a visible light image of the abnormality determination target captured by a visible light image capture device that captures the visible light image, acquire a reference visible light image obtained by capturing an image of the abnormality determination target in the reference state, and perform determination on the abnormality appearing in the outward appearance of the mammography apparatus on the basis of the distance image, the reference distance information, the visible light image, and the reference visible light image.

According to a tenth aspect of the present disclosure, in the information processing apparatus according to the ninth aspect, in a case in which it is determined that no abnormality has occurred in the outward appearance of the mammography apparatus on the basis of the distance image and the reference distance information and that an abnormality has occurred in the outward appearance of the mammography apparatus on the basis of the visible light image and the reference visible light image, the processor may determine that a stain has occurred as the abnormality.

According to an eleventh aspect of the present disclosure, in the information processing apparatus according to the first aspect, the reference distance information may be a reference distance image indicating a distance between the distance image capture device and the abnormality determination target disposed at a reference position.

According to a twelfth aspect of the present disclosure, in the information processing apparatus according to the eleventh aspect, in a case in which the abnormality determination target is not disposed at the reference position, after moving the abnormality determination target to the reference position, the processor may direct the distance image capture device to capture the distance image, and acquire the distance image captured by the distance image capture device.

According to a thirteenth aspect of the present disclosure, in the information processing apparatus according to the first aspect, the abnormality may be at least one of a scratch, a crack, deflection, or a stain.

According to a fourteenth aspect of the present disclosure, in the information processing apparatus according to the first aspect, the abnormality determination target may be a compression member that is attached to the mammography apparatus.

According to a fifteenth aspect of the present disclosure, in the information processing apparatus according to the first aspect, the abnormality determination target may be an imaging table of the mammography apparatus.

According to a sixteenth aspect of the present disclosure, in the information processing apparatus according to the first aspect, the abnormality determination target may be a biopsy-related member that is attached to the mammography apparatus.

According to a seventeenth aspect of the present disclosure, in the information processing apparatus according to the first aspect, the distance image capture device may capture the distance image using a time-of-flight (TOF) method.

Further, in order to achieve the above object, according to an eighteenth aspect of the present disclosure, there is provided an information processing method execute by a computer, the method comprising: acquiring a distance image which indicates a distance to an imaging target and is captured by a distance image capture device that captures the distance image using, as the imaging target, a mammography apparatus which is an abnormality determination target; acquiring reference distance information related to a reference value of a distance between the abnormality determination target in a reference state and the distance image capture device; and performing determination on an abnormality appearing in an outward appearance of the abnormality determination target on the basis of the distance image and the reference distance information.

Furthermore, in order to achieve the above object, according to a nineteenth aspect of the present disclosure, there is provided a non-transitory computer-readable storage medium storing an information processing program that causes a computer to perform a process comprising: acquiring a distance image which indicates a distance to an imaging target and is captured by a distance image capture device that captures the distance image using, as the imaging target, a mammography apparatus which is an abnormality determination target; acquiring reference distance information related to a reference value of a distance between the abnormality determination target in a reference state and the distance image capture device; and performing determination on an abnormality appearing in an outward appearance of the abnormality determination target on the basis of the distance image and the reference distance information.

According to the present disclosure, it is possible to perform determination on an abnormality occurring in the outward appearance of a mammography apparatus from a distance image.

BRIEF DESCRIPTION OF THE DRAWINGS

Exemplary embodiments according to the technique of the present disclosure will be described in detail based on the following figures, wherein.

DETAILED DESCRIPTION

Hereinafter, embodiments of the invention will be described in detail with reference to the drawings. Each of the embodiments does not limit the invention.

First Embodiment

Figure 1:
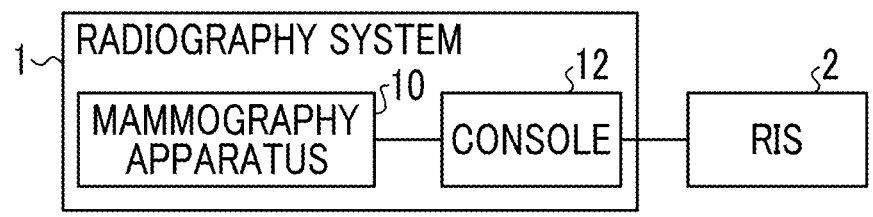
FIG. 1 is a schematic diagram illustrating an example of the overall configuration of a radiography system according to a first embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The console 12 according to this embodiment is an example of an information processing apparatus according to the present disclosure.

Figure 2:
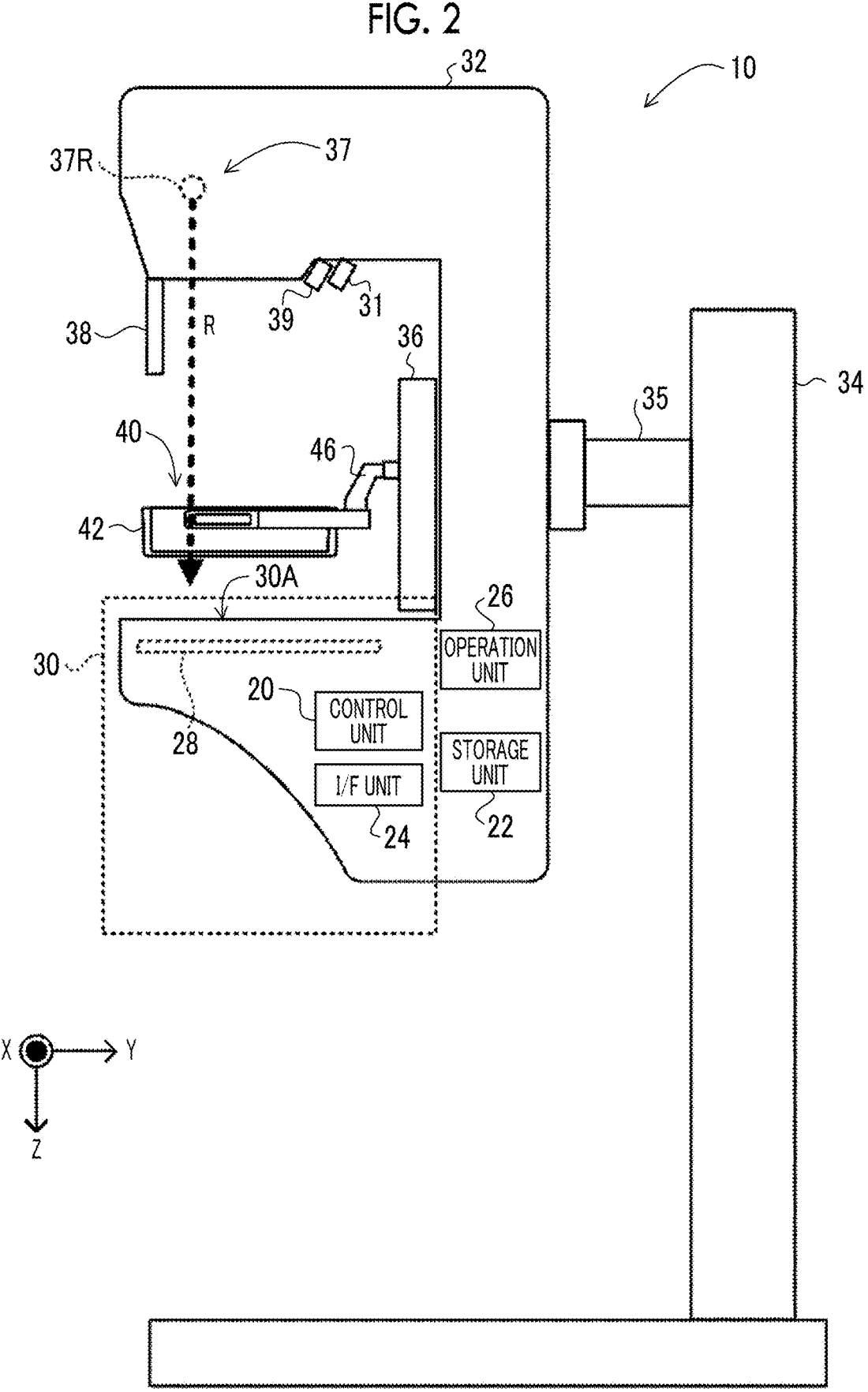
FIG. 2 is a side view illustrating an example of the outward appearance of a mammography apparatus according to the first embodiment.

First, the mammography apparatus 10 according to this embodiment will be described. FIG. 2 is a side view illustrating an example of the outward appearance of the mammography apparatus 10 according to this embodiment. In addition, FIG. 2 illustrates an example of the outward appearance of the mammography apparatus 10 as viewed from the right side of a subject.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of the breast of the subject not only in a state in which the subject stands up (standing state) but also in a state in which the subject sits on, for example, a chair (including a wheelchair) (sitting state).

As illustrated in FIG. 2, the mammography apparatus 10 according to this embodiment comprises a control unit 20, a storage unit 22, and an interface (I/F) unit 24 which are provided in an imaging table 30. The control unit 20 controls the overall operation of the mammography apparatus 10 under the control of the console 12. The control unit 20 comprises a central processing unit (CPU), a read only memory (ROM), and a random access memory (RAM) which are not illustrated. For example, various programs including an imaging processing program which is executed by the CPU and is used to perform control related to the capture of radiographic images are stored in the ROM in advance. The RAM temporarily stores various kinds of data.

For example, image data of the radiographic image captured by a radiation detector 28 and various other kinds of information are stored in the storage unit 22. Examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, an operation unit 26 is provided as a plurality of switches in, for example, the imaging table 30 of the mammography apparatus 10. Further, the operation unit 26 may be provided as a touch panel switch or may be provided as a foot switch that is operated by the user's feet.

The radiation detector 28 detects the radiation R transmitted through the breast which is the object. As illustrated in FIG. 2, the radiation detector 28 is disposed in the imaging table 30. In the mammography apparatus 10 according to this embodiment, in a case in which imaging is performed, the breast of the subject is positioned on an imaging surface 30A of the imaging table 30 by a user such as a doctor or a radiology technician.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R. As illustrated in FIG. 2, the radiation emitting unit 37 is provided in an arm portion 32 together with the imaging table 30 and a compression unit 36. As illustrated in FIG. 2, a face guard 38 is detachably attached to a position of the arm portion 32 which is close to the subject below the radiation emitting unit 37.

In addition, a visible light camera 31 and a time-of-flight (TOF) camera 39 are provided at a position of the arm portion 32 which is away from the subject below the radiation emitting unit 37. The visible light camera 31 is a so-called general camera and captures a visible light image. The visible light camera 31 according to this embodiment is an example of a visible light image capture device according to the present disclosure. Specifically, the visible light camera 31 receives visible light reflected by an imaging target and captures a visible light image on the basis of the received visible light.

The TOF camera 39 is a camera that captures a distance image indicating a distance to the imaging target using a TOF method. The TOF camera 39 according to this embodiment is an example of a distance image capture device according to the present disclosure. Specifically, the TOF camera 39 emits light, such as infrared rays, to the imaging target and measures the distance between the TOF camera 39 and the imaging target on the basis of the time until reflected light is received or a phase change between the emitted light and the received light. In the distance image captured by the TOF camera 39, each pixel has distance information indicating the distance between the TOF camera 39 and the imaging target. Further, the distance image is an image from which the distance to the imaging target can be derived.

In addition, the imaging target in this embodiment is the mammography apparatus 10 whose abnormality is to be determined (hereinafter, referred to as an "abnormality determination target"), which will be described in detail below. The abnormality determination target is not limited to the entire mammography apparatus 10, and may be a part, such as the imaging table 30, or a component, such as a compression plate 40, in the mammography apparatus 10. Therefore, a region including the abnormality determination target is an imaging region of the TOF camera 39. In addition, in the TOF camera 39 and the visible light camera 31, the imaging targets are the same, but the imaging regions may not be exactly the same.

In addition, as illustrated in FIG. 2, the mammography apparatus 10 according to this embodiment comprises the arm portion 32, a base 34, and a shaft portion 35. The arm portion 32 is held by the base 34 so as to be movable in the up-down direction (Z-axis direction). The shaft portion 35 connects the arm portion 32 to the base 34. In addition, the arm portion 32 can be relatively rotated with respect to the base 34, using the shaft portion 35 as a rotation axis.

Each of the arm portion 32 and the compression unit 36 can be relatively rotated with respect to the base 34, using the shaft portion 35 as a rotation axis. In this embodiment, gears (not illustrated) are provided in each of the shaft portion 35, the arm portion 32, and the compression unit 36. Each gear is switched between an engaged state and a disengaged state to connect each of the arm portion 32 and the compression unit 36 to the shaft portion 35. One or both of the arm portion 32 and the compression unit 36 connected to the shaft portion 35 are rotated integrally with the shaft portion 35.

The compression unit 36 is provided with a compression plate driving unit (not illustrated) that moves a compression plate 40 in the up-down direction (Z-axis direction). The compression plate 40 according to this embodiment has a function of compressing the breast of the subject. A support portion 46 of the compression plate 40 is detachably attached to the compression plate driving unit and is moved in the up-down direction (Z-axis direction) by the compression plate driving unit to compress the breast of the subject between the compression plate 40 and the imaging table 30. The compression plate 40 according to this embodiment is an example of a compression member according to the present disclosure.

There are a plurality of types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 is known which is used for so-called spot imaging that captures a radiographic image of only the region in which a lesion is present. Further, other types of compression plates 40 include, for example, a compression plate corresponding to the size of the breast, a compression plate for axillary imaging, and a compression plate for magnification imaging.

Figure 3:
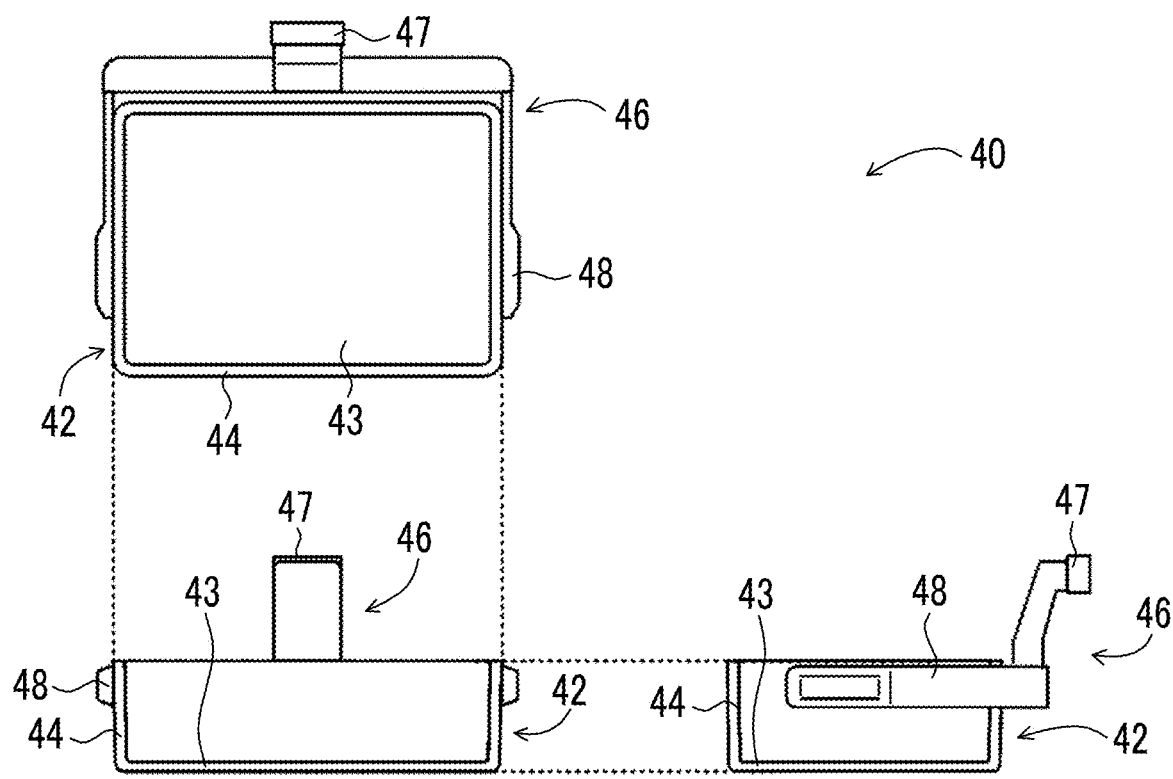
FIG. 3 is a three-view diagram illustrating an example of a compression plate according to the first embodiment.

As a specific example, the compression plate 40 attached to the mammography apparatus 10 according to this embodiment will be described with reference to FIG. 3. FIG. 3 is a three-view diagram illustrating an example of the compression plate 40 according to this embodiment. The three-view diagram illustrated in FIG. 3 includes a plan view (top view) of the compression plate 40 viewed from the upper side (from the radiation emitting unit 37), a side view of the compression plate 40 viewed from the subject, and a side view of the compression plate 40 viewed from the right side of the subject. As illustrated in FIG. 3, the compression plate 40 according to this embodiment includes a compression portion 42 and a support portion 46.

The compression portion 42 is formed in a concave shape in a cross-sectional view in which a bottom portion 43 is surrounded by a wall portion 44. In the bottom portion 43, the thickness of a plate having a surface that comes into contact with the breast of the subject is substantially constant. It is preferable that the compression portion 42 is optically transparent in order to check positioning or a compressed state in the compression of the breast. In addition, the compression portion 42 is made of a material having high transmittance for the radiation R. Specific examples of the material include polycarbonate (PC) and polyethylene terephthalate (PRT), acrylic, and polypropylene (PP). However, the material is not particularly limited.

On the other hand, the support portion 46 includes an attachment portion 47 and an arm 48. The attachment portion 47 has a function of attaching the compression plate 40 to the mammography apparatus 10, specifically, the compression plate driving unit in the compression plate 40. The arm 48 has a function of supporting the compression portion 42.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

Figure 4:
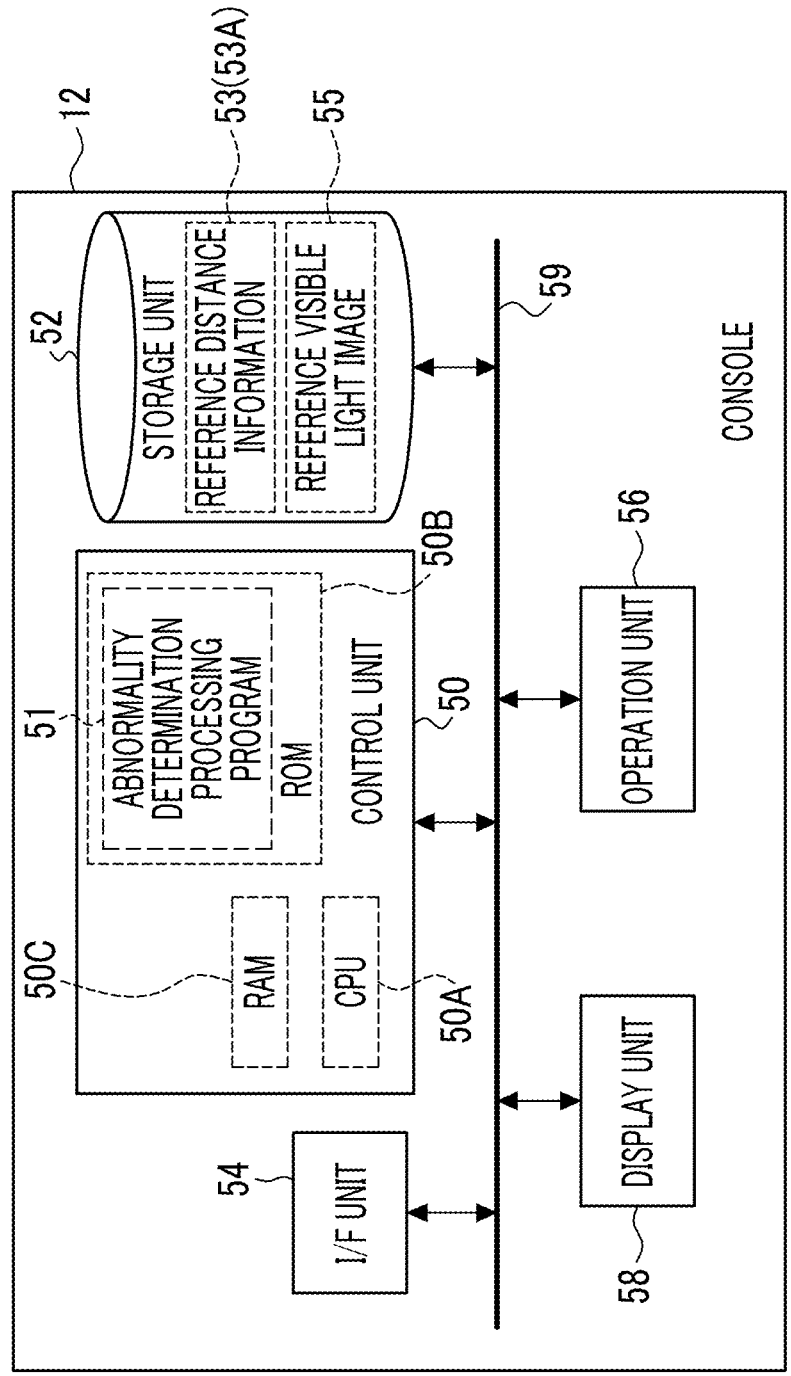
FIG. 4 is a block diagram illustrating an example of the configuration of a console according to the first embodiment.

For example, the console 12 according to this embodiment is a server computer. As illustrated in FIG. 4, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including an abnormality determination processing program 51 executed by the CPU 50A are stored in the ROM 50B in advance. The RAM 50C temporarily stores various kinds of data. The CPU 50A according to this embodiment is an example of a processor according to the present disclosure, and the ROM 50B according to this embodiment is an example of a memory according to the present disclosure. Further, the abnormality determination processing program 51 according to this embodiment is an example of an information processing program according to the present disclosure.

For example, the image data of the radiographic image captured by the mammography apparatus 10 and various other kinds of information are stored in the storage unit 52. An HDD or an SSD is given as a specific example of the storage unit 52. Further, the storage unit 52 according to this embodiment stores reference distance information 53 which will be described in detail below.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 5:
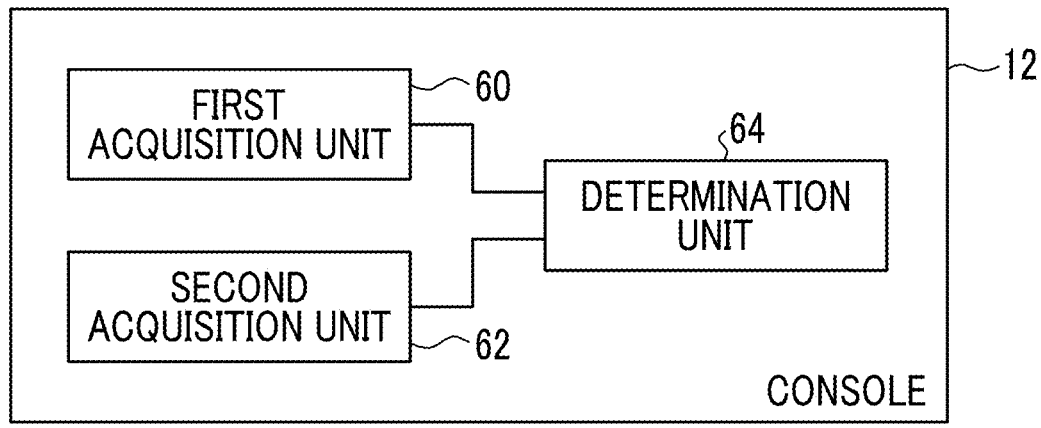
FIG. 5 is a functional block diagram illustrating an example of the functional configuration of the console according to the first embodiment.

FIG. 5 is a functional block diagram illustrating an example of the configuration of the console 12 according to this embodiment. As illustrated in FIG. 5, the console 12 comprises a first acquisition unit 60, a second acquisition unit 62, and a determination unit 64. For example, in the console 12 according to this embodiment, the CPU 50A of the control unit 50 executes the abnormality determination processing program 51 stored in the ROM 50B to function as the first acquisition unit 60, the second acquisition unit 62, and the determination unit 64.

The first acquisition unit 60 has a function of acquiring the distance image captured by the TOF camera 39. For example, the first acquisition unit 60 according to this embodiment acquires image data indicating the distance image captured by the TOF camera 39 from the TOF camera 39 through the I/F unit 24 and the I/F unit 54.

In addition, the first acquisition unit 60 has a function of acquiring the visible light image captured by the visible light camera 31. For example, the first acquisition unit 60 according to this embodiment acquires image data indicating the visible light image captured by the visible light camera 31 from the visible light camera 31 through the I/F unit 24 and the I/F unit 54.

The second acquisition unit 62 has a function of acquiring the reference distance information 53. For example, the second acquisition unit 62 according to this embodiment acquires the reference distance information 53 from the storage unit 52. The reference distance information 53 is information related to a reference value of the distance between the abnormality determination target and the TOF camera 39 in a state in which the abnormality determination target in a reference state is disposed at a reference position. For example, in a case in which the abnormality determination target is the compression plate 40, the reference distance information 53 is information related to the reference value of the distance between the TOF camera 39 and the compression plate 40 in an initial state which is attached to the initial position of the mammography apparatus 10. In addition, an example of the initial position in the disposition of the compression plate 40 is the position where the compression plate 40 is closest to the imaging table 30. Further, an example of the initial state of the compression plate 40 is an unused state. Furthermore, an example of the reference distance information 53 is a distance image captured by the TOF camera 39. Hereinafter, the distance image as the reference distance information 53 is referred to as a reference distance image 53A.

In addition, the second acquisition unit 62 has a function of acquiring a reference visible light image 55. For example, the second acquisition unit 62 according to this embodiment acquires the reference visible light image 55 from the storage unit 52. The reference visible light image 55 is a visible light image captured by the visible light camera 31 in a state in which the abnormality determination target in the reference state is disposed at the reference position. In addition, the reference state and the reference position in this case are the same as the reference state and the reference position for the reference distance information 53.

As described above, in this embodiment, the aspect in which the reference distance information 53 and the reference visible light image 55 are stored in the storage unit 52 of the console 12 has been described. However, the place in which the reference distance information 53 and the reference visible light image 55 are stored is not limited to the storage unit 52. For example, the reference distance information 53 and the reference visible light image 55 may be stored in the storage unit 22 of the mammography apparatus 10 or may be stored in a device outside the radiography system 1. In addition, the reference distance information 53 and the reference visible light image 55 may be stored in different devices.

Further, in this embodiment, in a case in which the mammography apparatus 10 which is the abnormality determination target is described with a specific example, the compression plate 40 will be described as an example. In this case, the reference distance information 53 is the reference distance image 53A captured by the TOF camera 39 in a state in which the unused compression plate 40 is attached to the mammography apparatus 10 for the first time and is disposed at the position closest to the imaging table 30. Further, the reference visible light image 55 is the reference visible light image captured by the visible light camera 31 in a state in which the unused compression plate 40 is attached to the mammography apparatus 10 for the first time and is disposed at the position closest to the imaging table 30.

The determination unit 64 has a function of determining an abnormality appearing in the outward appearance of the mammography apparatus 10 on the basis of the distance image, the reference distance information 53, the visible light image, and the reference visible light image 55. In addition, the abnormality determination target may not be the entire mammography apparatus 10 and may be parts or components (hereinafter, simply referred to as "components") of the mammography apparatus 10 such as the compression plate 40, the imaging table 30, a biopsy-related member, and the face guard. Further, in a case in which the abnormality determination target is a component of the mammography apparatus 10, a plurality of components may be the abnormality determination targets. For example, both the compression plate 40 and the imaging table 30 may be the abnormality determination targets. In this case, the images of the compression plate 40 and the imaging table 30 as the abnormality determination targets are simultaneously captured, which makes it possible to determine abnormalities for a plurality of abnormality determination targets using one distance image.

Here, a method for determining an abnormality appearing in the outward appearance of the mammography apparatus 10 on the basis of the distance image, the reference distance information 53, the visible light image, and the reference visible light image 55 in the determination unit 64 according to this embodiment will be described. The determination unit 64 according to this embodiment determines whether or not an abnormality, such as a scratch, a crack, deflection, or a stain, has occurred as an example of the abnormality appearing in the outward appearance of the mammography apparatus 10 (hereinafter, simply referred to as an "abnormality"). In a case in which the abnormality has occurred, the determination unit 64 determines the position where the abnormality has occurred.

Figure 6A:
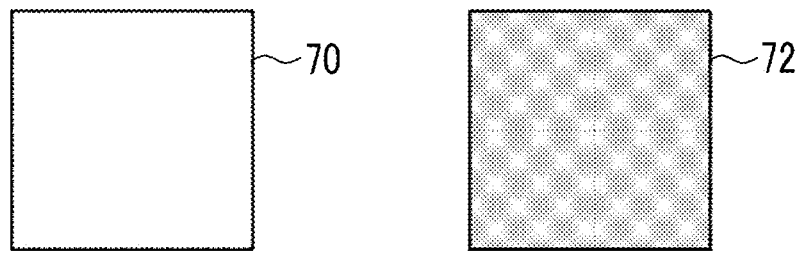
FIG. 6A is a diagram illustrating an example of a visible light image and a distance image in a case in which no abnormality has occurred.

FIG. 6A illustrates an example of a visible light image 70 and a distance image 72 obtained by capturing a state in which no abnormality occurs. The visible light image 70 does not include an image showing a scratch, a crack, deflection, and a stain which are abnormalities. Further, the distance image 72 does not show any abnormality. As such, in a case in which no abnormality has occurred in the abnormality determination target, the distance image 72 is a distance image showing the distance to the abnormality determination target. For example, in a case in which the abnormality determination target is a flat plate, the distance to the abnormality determination target is uniform. Therefore, the distance image 72 is an image in which pixel values are substantially uniform.

Figure 6B:
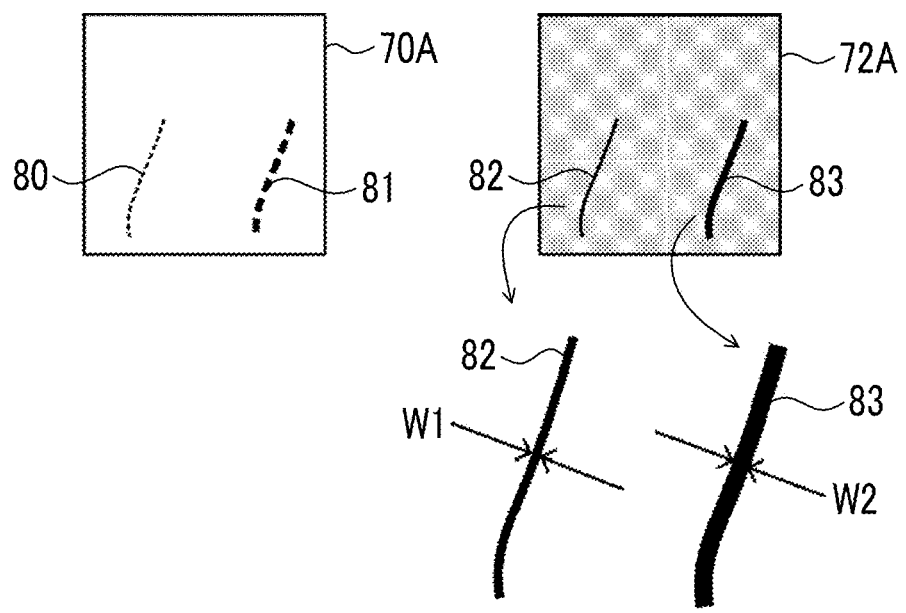
FIG. 6B is a diagram illustrating an example of a visible light image and a distance image in a case in which a crack or a scratch has occurred as an abnormality.

FIG. 6B illustrates an example of a visible light image 70A and a distance image 72A obtained by capturing a state in which a scratch or a crack occurs. The visible light image 70A includes a crack image 80 and a scratch image 81. Further, in FIG. 6B, the crack image 80 and the scratch image 81 are represented by dotted lines. However, the crack image 80 and the scratch image 81 are represented by the dotted lines for convenience of illustration and are not the images of the crack and scratch on the dotted lines. The specific conditions of the crack and the scratch do not matter. Furthermore, the distance image 72A includes an abnormal region 82 corresponding to the crack and an abnormal region 83 corresponding to the scratch.

In a case in which there is a crack or a scratch, the infrared rays emitted to the abnormality determination target in the capture of the distance image by the TOF camera 39 are diffusely reflected by the crack or the scratch and do not accurately reach the TOF camera 39. As a result, in a portion corresponding to the crack or scratch, the distance to the abnormality determination target measured by the TOF camera 39 tends to be longer than the actual distance. Therefore, in the portion corresponding to the crack or scratch, the distance measured by the TOF camera 39 tends to be longer than the distance measured in a case in which the abnormality determination target is in the normal state. In addition, the distance to the portion corresponding to the crack or scratch is longer than the distance to a portion in the normal state which is present around the crack or the scratch.

Figure 6C:
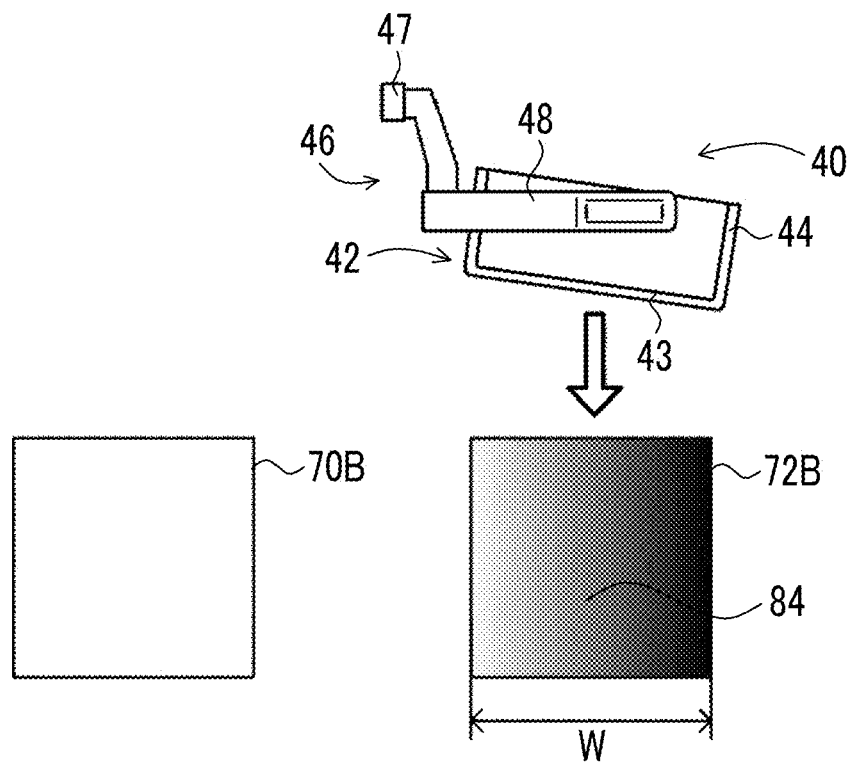
FIG. 6C is a diagram illustrating an example of a visible light image and a distance image in a case in which deflection has occurred as an abnormality.

FIG. 6C illustrates an example of a visible light image 70B and a distance image 72B obtained by capturing a state in which deflection occurs. The deflection may also be distortion and is accompanied by deformation such as plastic deformation in the abnormality determination target. However, as in the visible light image 70B, a visible light image may not show deformation caused by the deflection. In contrast, in the distance image 72B, a region deformed by the deflection appears as an abnormal region 84. For example, in a case in which the entire compression portion 42 of the compression plate 40 is deflected as illustrated in FIG. 6C, the distance image 72B obtained by capturing the bottom portion 43 includes the abnormal region 84 corresponding to the deflection.

In a case in which the compression portion 42 is deformed in a direction in which it becomes closer to the TOF camera 39 due to the deflection, the distance between the abnormality determination target and the TOF camera 39 is shorter than the distance measured in the normal state in which the deformation caused by the deflection does not occur. On the contrary, in a case in which the compression portion 42 is deformed in a direction in which it becomes further away from the TOF camera 39 due to the deflection, the distance between the abnormality determination target and the TOF camera 39 is longer than the distance measured in the normal state in which the deformation caused by the deflection does not occur.

In addition, in a case in which the compression portion 42 is deformed in a direction parallel to the TOF camera 39, the position of a feature point of the abnormality determination target in the height direction, that is, a feature point in the distance to the TOF camera 39 changes. For example, in a case in which the bottom portion 43 of the compression plate 40 (see FIG. 3) changes from a rectangle to a parallelogram, the position of the wall portion 44 which is a feature point changes. Therefore, in a portion corresponding to the position of the wall portion 44 before and after the deformation caused by the deflection, the distance between the abnormality determination target and the TOF camera 39 is longer or shorter than the distance measured in the normal state in which the deformation caused by the deflection does not occur.

As such, the distance images 72A and 72B show the abnormal regions 82, 83, and 84 corresponding to the abnormalities, regardless of whether the abnormality is a crack, a scratch, or deflection. However, the abnormal region caused by the deflection tends to be larger and wider than the abnormal region caused by the crack and the abnormal region caused by the scratch. In many cases, cracks and scratches occur linearly. In this case, as illustrated in FIG. 6B, the abnormal regions 82 and 83 are long and thin regions. Assuming that directions intersecting the length directions of the long abnormal regions 82 and 83 are widths W1 and W2, respectively, each of the widths W1 and W2 is smaller than a width W3 (see FIG. 6C) of the abnormal region 84 caused by the deflection.

Therefore, in a case in which the determination unit 64 according to this embodiment has compared the distance image captured by the TOF camera 39 with the reference distance image 53A and specified an abnormal region from the distance image, it determines that any abnormality of a crack, a scratch, or deflection has occurred. Specifically, in a case in which the absolute value of a difference between the distance indicated by the distance image and the distance indicated by the reference distance image 53A is greater than an abnormality determination threshold value, that is, in a case in which the amount of change in the distance to the TOF camera 39 is large, the determination unit 64 according to this embodiment determines that any abnormality of a crack, a scratch, or deflection has occurred. More specifically, in a case in which the absolute value of a difference between the pixel value of a pixel in the distance image and the pixel value of a pixel in the reference distance image 53A is greater than the abnormality determination threshold value, the determination unit 64 determines that any abnormality of a crack, a scratch, or deflection has occurred. In addition, for example, a value which has been experimentally obtained using the distance images obtained by capturing various cracks, scratches, deflections, and the like with the TOF camera 39 in consideration of a normal state, errors, or the like can be used as the abnormality determination threshold value.

Further, in a case in which the width of the abnormal region is equal to or greater than a type determination threshold value, the determination unit 64 according to this embodiment determines that the type of abnormality which has occurred is deflection. On the other hand, in a case in which the width of the abnormal region is less than the type determination threshold value, the determination unit 64 determines that the type of the abnormal surface which has occurred is a crack or a scratch. In addition, for example, a value which has been experimentally obtained on the basis of the width of the abnormal region caused by the crack or the scratch included in the distance image obtained by capturing various cracks, scratches, deflections, and the like with the TOF camera 39 and the width of the abnormal region caused by the deflection can be used as the type determination threshold value.

Figure 6D:
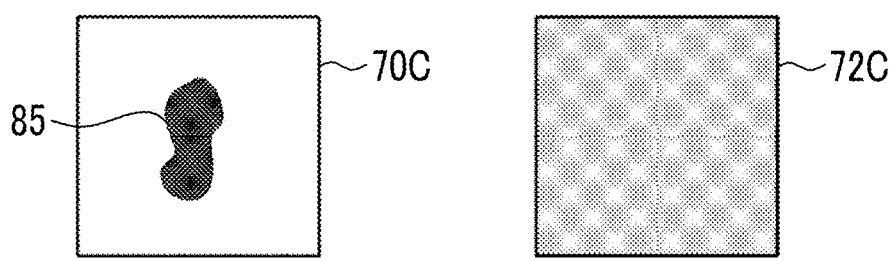
FIG. 6D is a diagram illustrating an example of a visible light image and a distance image in a case in which a stain has occurred as an abnormality.

FIG. 6D illustrates an example of a visible light image 70C and a distance image 72C obtained by capturing a state in which a stain occurs. The visible light image 70C includes a stain image 85. In contrast, the distance image 72C does not include an abnormal region regardless of the stain. The stain that occurs in the abnormality determination target does not cause unevenness on the surface. Alternatively, even in a case in which unevenness occurs, it is relatively little. Therefore, in a portion corresponding to the stain, the distance measured by the TOF camera 39 tends to be substantially the same as the distance measured in a case in which the abnormality determination target is in the normal state, and a change in the distance between the abnormality determination target and the TOF camera 39 tends to be smaller than that at least in a case in which the other abnormalities have occurred.

Therefore, the determination unit 64 according to this embodiment determines that a stain has occurred as an abnormality in a case in which the result of the comparison between the distance image captured by the TOF camera 39 and the reference distance image 53A shows that the distance image does not include an abnormal region and the result of the comparison between the visible light image captured by the visible light camera 31 and the reference visible light image 55 shows that an abnormality has occurred. Specifically, the determination unit 64 according to this embodiment determines that no cracks, scratches, and deflections have occurred as abnormalities in a case in which the absolute value of the difference between the distance represented by the distance image and the distance represented by the reference distance image 53A is equal to or less than the abnormality determination threshold value, that is, the amount of change in the distance to the TOF camera 39 is small. Further, in the determination unit 64 determines that a stain has occurred as an abnormality in a case in which the number of consecutive pixels satisfying the condition that the absolute value of the difference between the pixel value of the pixel in the visible light image and the pixel value of the pixel in the reference visible light image 55 is greater than a stain determination threshold value, is equal to or greater than a value required for stain determination. In this case, the region of the stain image 85 in the visible light image 70C is an abnormal region.

Further, the determination unit 64 according to this embodiment determines that no abnormalities have occurred in a case in which the result of the comparison between the distance image captured by the TOF camera 39 and the reference distance image 53A shows that an abnormal region is not included in the distance image and the result of the comparison between the visible light image captured by the visible light camera 31 and the reference visible light image 55 shows that there is no abnormality.

Next, the operation of the console 12 according to this embodiment will be described with reference to the drawings.

Figure 7:
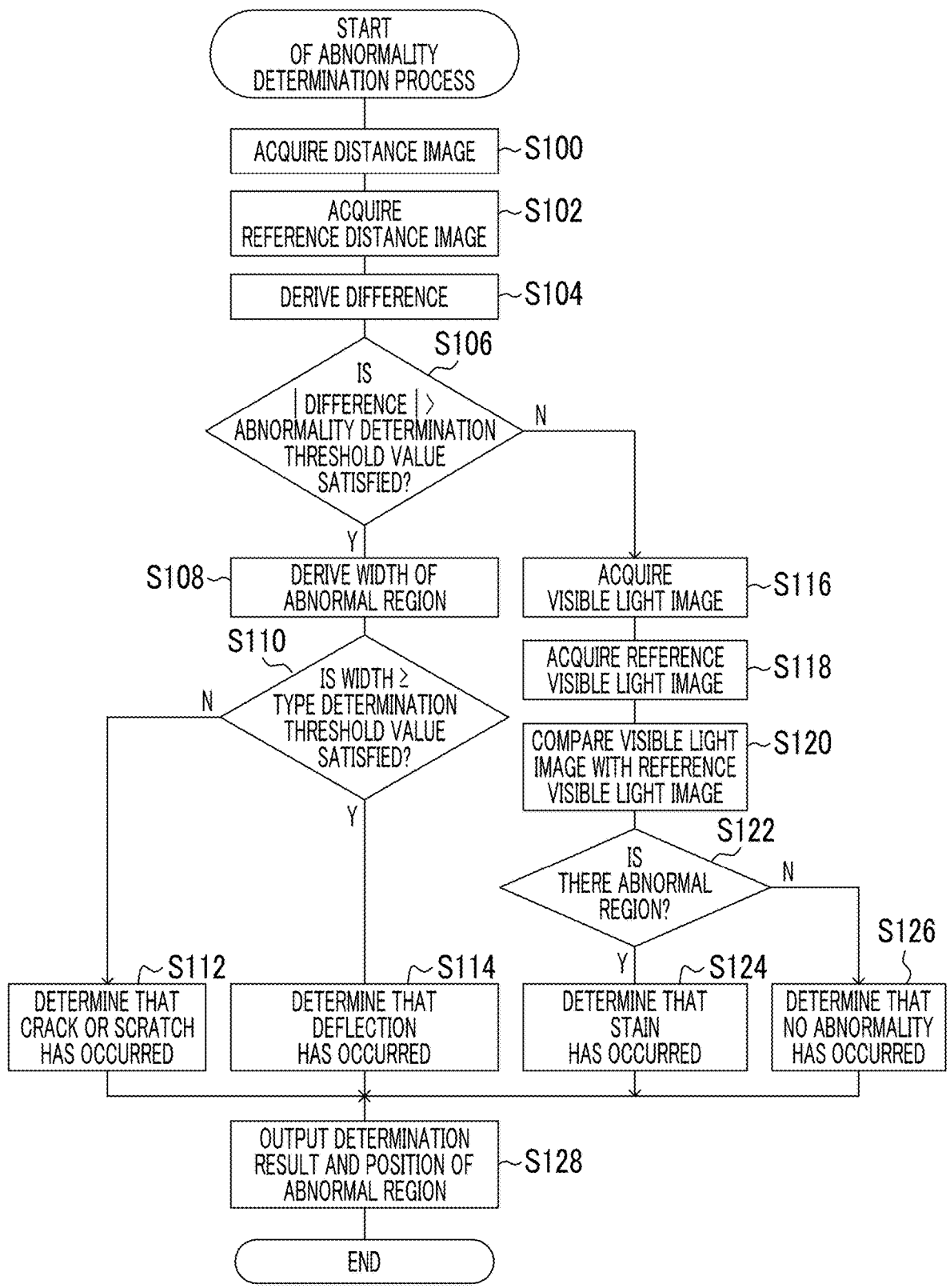
FIG. 7 is a flowchart illustrating an example of the flow of an abnormality determination process of the console according to the first embodiment.

In the console 12 according to this embodiment, the CPU 50A of the control unit 50 executes the abnormality determination processing program 51 stored in the ROM 50B to perform an abnormality determination process whose example is illustrated in FIG. 7. FIG. 7 is a flowchart illustrating an example of the flow of the abnormality determination process performed in the console 12 according to this embodiment. In addition, the timing when the CPU 50A performs the abnormality determination process is not limited, and the CPU 50A may perform the abnormality determination process at any timing. For example, the CPU 50A may perform the abnormality determination process whenever a predetermined time has elapsed since the first operation of the mammography apparatus 10, the timing when the mammography apparatus 10 is turned on, or the timing when an instruction issued by the user through the operation unit 56 is received. Further, for example, in the case of the compression plate 40, the CPU 50A may perform the abnormality determination process at the timing when the compression plate 40 is attached to the mammography apparatus 10.

In Step S100 of FIG. 7, the first acquisition unit 60 acquires a distance image from the TOF camera 39 of the mammography apparatus 10. Specifically, the first acquisition unit 60 instructs the TOF camera 39 to capture a distance image and acquires the distance image captured by the TOF camera 39 on the basis of the instruction through the I/F unit 24. The distance image acquired by the first acquisition unit 60 is output to the determination unit 64.

In addition, in a case in which the abnormality determination target is not disposed at the reference position at this timing, it is preferable that the determination unit 64 moves the abnormality determination target to the reference position and then instructs the TOF camera 39 to capture a distance image. For example, in a case in which the abnormality determination target is the compression plate 40, the determination unit 64 specifies the position of the attachment portion 47 attached to the compression unit 36 to specify the current position of the compression plate 40. In a case in which the current position is not the reference position, the determination unit 64 instructs the mammography apparatus 10 to move the compression plate 40 to the reference position. The control unit 20 of the mammography apparatus 10 that has received the instruction moves the compression plate 40 to the reference position using the compression unit 36. After checking that the current position of the compression plate 40 is the reference position, the determination unit 64 instructs the TOF camera 39 to capture a distance image.

Then, in Step S102, the second acquisition unit 62 acquires the reference distance information 53 from the storage unit 52. As described above, in this embodiment, the reference distance image 53A is adopted as the reference distance information 53. Therefore, the reference distance image 53A is acquired from the storage unit 52. The acquired reference distance image 53A is output to the determination unit 64.

Then, in Step S104, the determination unit 64 derives the difference between the distance image and the reference distance image 53A. Specifically, as described above, for the pixels at the corresponding positions, the difference between the pixel value of the pixel in the distance image and the pixel value of the pixel in the reference distance image 53A is derived.

Then, in Step S106, as described above, the determination unit 64 determines whether or not the absolute value of the difference derived in the Step S104 is greater than the abnormality determination threshold value (|difference|>the abnormality determination threshold value). In a case in which the absolute value of the difference is greater than the abnormality determination threshold value, the determination result in Step S106 is "Yes", and the process proceeds to Step S108.

In Step S108, the determination unit 64 derives the width of the abnormal region as described above. Then, in Step S110, as described above, the determination unit 64 determines whether or not the width of the abnormal region derived in Step S108 is equal to or greater than the type determination threshold value (the width≥the type determination threshold value). In a case in which the width of the abnormal region is not equal to or greater than the type determination threshold value, that is, in a case in which the width of the abnormal region is less than the type determination threshold value, the determination result in Step S110 is "No", and the process proceeds to Step S112. As described above, the determination unit 64 determines that a crack or a scratch has occurred as an abnormality in Step S112 and then proceeds to Step S128.

On the other hand, in a case in which the width of the abnormal region is equal to or greater than the type determination threshold value in Step S110, the determination result is "Yes", and the process proceeds to Step S114. As described above, the determination unit 64 determines that deflection has occurred as an abnormality in Step S114 and then proceeds to Step S128.

Further, in a case in which the absolute value of the difference derived in Step S104 is not greater than the abnormality determination threshold value, that is, in a case in which the absolute value of the difference is equal to or less than the abnormality determination threshold value in Step S106, the determination result in Step S106 is "No", and the process proceeds to Step S116.

In Step S116, the first acquisition unit 60 acquires a visible light image from the visible light camera 31 of the mammography apparatus 10. Specifically, the first acquisition unit 60 instructs the visible light camera 31 to capture a visible light image and acquires the visible light image captured by the visible light camera 31 on the basis of the instruction through the I/F unit 24. The visible light image acquired by the first acquisition unit 60 is output to the determination unit 64.

Then, in Step S118, the second acquisition unit 62 acquires the reference visible light image 55 from the storage unit 52. As described above, the acquired reference visible light image 55 is output to the determination unit 64. Then, in Step S120, the determination unit 64 compares the visible light image with the reference visible light image as described above.

Then, in Step S122, the determination unit 64 determines whether or not an abnormal region is included in the visible light image as described above. In a case in which an abnormal region is included in the visible light image, the determination result in Step S122 is "Yes", and the process proceeds to Step S124. In Step S124, as described above the determination unit 64 determines that a stain has occurred as an abnormality and then proceeds to Step S128.

On the other hand, in a case in which an abnormal region is not included in the visible light image in Step S122, the determination result is "No", and the process proceeds to Step S126. In Step S126, as described above, the determination unit 64 determines that no abnormality has occurred and then proceeds to Step S128.

In Step S128, the determination unit 64 outputs the determination result and the position of the abnormal region. Specifically, the determination unit 64 outputs any of the determination results in Steps S112, S114, S124, and S126. Further, the determination unit 64 outputs the position of the abnormal region in a case in which the determination results in Steps S112, S114, and S124 are output. In addition, the output aspect of the position of the abnormal region is not particularly limited. For example, an image obtained by adding information indicating the position of a specified abnormal region to the visible light image may be output. Furthermore, the output destination of the determination results and the position of the abnormal region by the determination unit 64 is not particularly limited. For example, the output destination may be the display unit 58 of the console 12, the mammography apparatus 10, or other apparatuses. In a case in which the process in Step S128 ends in this way, the abnormality determination process illustrated in FIG. 7 ends.

The present disclosure is not limited to this aspect. The timing when the TOF camera 39 captures the distance image, the timing when the visible light camera 31 captures the visible light image, and the timing when the CPU 50A performs the abnormality determination process may not be synchronized with each other. For example, the TOF camera 39 may capture the distance image at any timing. The visible light camera 31 may capture the visible light image. The distance image and the visible light image may be stored in the storage unit 22. The CPU 50A may acquire the distance image and the visible light image stored in the storage unit 22 and perform the abnormality determination process at any another timing.

As described above, in a case in which the abnormality is any of a crack, a scratch, or deflection, the abnormality appears as an abnormal region in the distance image. In addition, in a case in which the abnormality is a stain, the abnormality appears in the visible light image. Therefore, in this embodiment, the console 12 acquires the distance image captured by the TOF camera 39 and the visible light image captured by the visible light camera 31 and determines an abnormality occurring in the outward appearance of the mammography apparatus 10 which is the abnormality determination target, on the basis of the distance image, the reference distance image 53A, the visible light image, and the reference visible light image 55. Therefore, the console 12 according to this embodiment can determine an abnormality occurring in the outward appearance of the mammography apparatus from the distance image.

Second Embodiment

As described above, the mammography apparatus 10 has a plurality of components, and each of the plurality of components can be used as the abnormality determination target. As such, in a case in which each of the plurality of components is used as the abnormality determination target, the normal state and the degree of occurrence of abnormalities may vary depending on the components. Therefore, in this embodiment, an aspect in which abnormality determination is performed on each of the plurality of components will be described. For a mammography apparatus 10 and a console 12 according to this embodiment, the detailed description of the same configuration and operation as those in the first embodiment will not be repeated.

Figure 8:
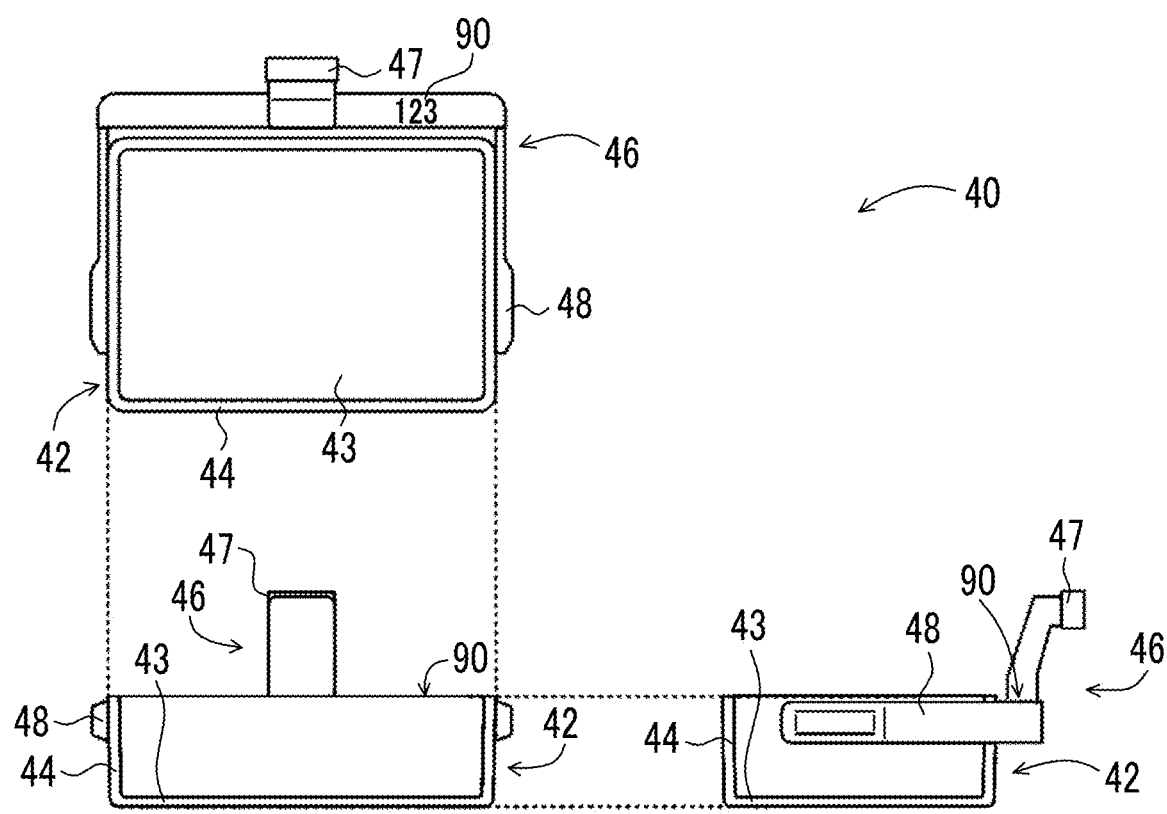
FIG. 8 is a diagram illustrating an example of identification information given to a compression plate.

Since the overall configuration of the mammography apparatus 10 and the console 12 according to this embodiment is the same as that in the first embodiment, the description of the overall configuration will not be repeated. In the mammography apparatus 10 according to this embodiment, identification information for identifying each abnormality determination target is given to each abnormality determination target. FIG. 8 illustrates an example of the compression plate 40 to which identification information 90 is given. In the compression plate 40 illustrated in FIG. 8, the identification information 90 is provided at a position that faces the radiation emitting unit 37 in the arm 48 that extends from the attachment portion 47. The identification information 90 is information for identifying the compression plate. Further, there are a plurality of types of compression plates 40 that can be attached to the mammography apparatus 10 according to this embodiment. Therefore, the identification information 90 is also information for identifying the type of the compression plate 40. Moreover, even in a case in which the same components and the same type are used, the normal state may vary depending on each component. In this case, the identification information 90 may be identification information for identifying each component, or different identification information items 90 may be given to the components.

In this embodiment, for example, the identification information 90 given to the abnormality determination target is read from the visible light image captured by the visible light camera 31. Therefore, the position where the identification information 90 is given to the abnormality determination target is a position in the imaging region of the visible light camera 31 and is a position where the identification information 90 is given to the visible light camera 31. Further, as described above, the normal state and the degree of occurrence of abnormalities may vary depending on the components. Therefore, in this embodiment, the abnormality determination threshold value is provided for each component which is the abnormality determination target. Therefore, in this embodiment, the abnormality determination threshold value associated with the identification information 90 is stored in the storage unit 22 (not illustrated).

Further, in this embodiment, the reference distance image 53A and the reference visible light image 55 are also stored for each abnormality determination target in the storage unit 52. Specifically, a plurality of reference distance images 53A and reference visible light images 55 associated with each identification information item 90 are stored in the storage unit 22 of the console 12.

In addition, since the operation of the console 12, specifically, the abnormality determination process is different from that in the first embodiment, the abnormality determination process performed by the console 12 according to this embodiment will be described.

Figure 9:
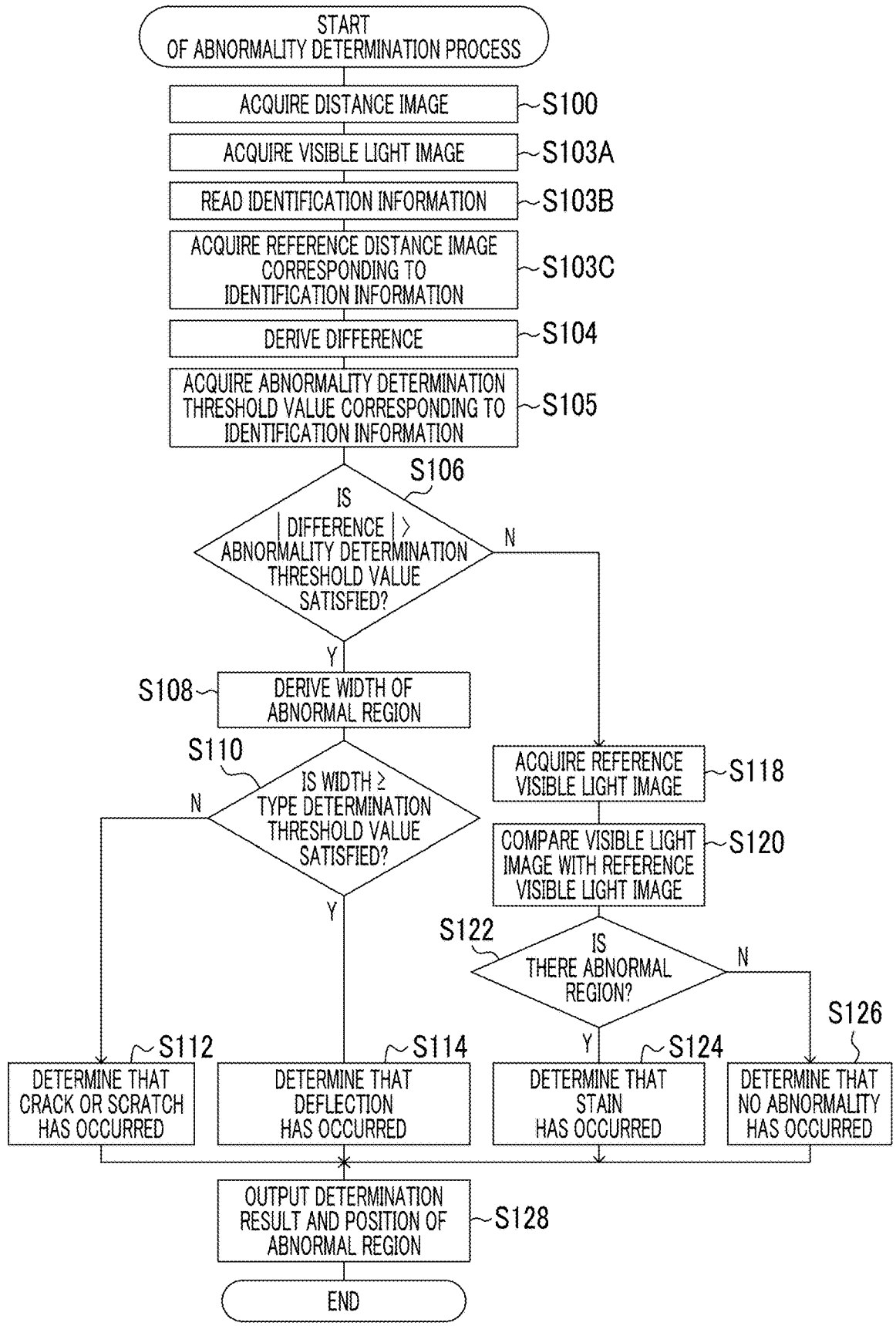
FIG. 9 is a flowchart illustrating an example of the flow of an abnormality determination process of a console according to a second embodiment.

FIG. 9 is a flowchart illustrating an example of the flow of the abnormality determination process performed in the console 12 according to this embodiment. As illustrated in FIG. 9, the abnormality determination process according to this embodiment includes a process in Steps S103A to S103C instead of Step S102 in the abnormality determination process (see FIG. 7) according to the first embodiment.

In Step S103A illustrated in FIG. 9, the first acquisition unit 60 acquires a visible light image from the visible light camera 31 of the mammography apparatus 10 in the same manner as in Step S116 of the abnormality determination process (see FIG. 7) according to the first embodiment. Further, in the abnormality determination process according to this embodiment, the visible light image is acquired at this timing. Therefore, as illustrated in FIG. 9, the abnormality determination process according to this embodiment does not include the process in Step S116 which is a step for acquiring the visible light image in the abnormality determination process (see FIG. 7) according to the first embodiment.

Then, in Step S103B, the determination unit 64 reads the identification information from the visible light image. In addition, a method for reading the identification information from the visible light image in the determination unit 64 is not particularly limited. For example, in a case in which the identification information is a number or a letter like the identification information 90 illustrated in FIG. 8, the determination unit 64 may perform image analysis for reading the number or the letter on the visible light image and read the number or the letter from the image of a portion corresponding to the abnormality determination target to read the identification information 90.

Then, in Step S103C, the determination unit 64 acquires the reference distance image 53A corresponding to the identification information read in Step S103B from the storage unit 22. In the subsequent process, the reference distance image 53A acquired in this step is used for abnormality determination.

Further, as illustrated in FIG. 9, the abnormality determination process according to this embodiment includes a process in Step S105 between the process in Step S104 and the process in Step S106 of the abnormality determination process (see FIG. 7) according to the first embodiment.

In Step S105, the determination unit 64 acquires an abnormality determination threshold value corresponding to the identification information read in Step S103B from the storage unit 22. In the subsequent process, the abnormality determination threshold value acquired in this step is used for abnormality determination.

Figure 10:
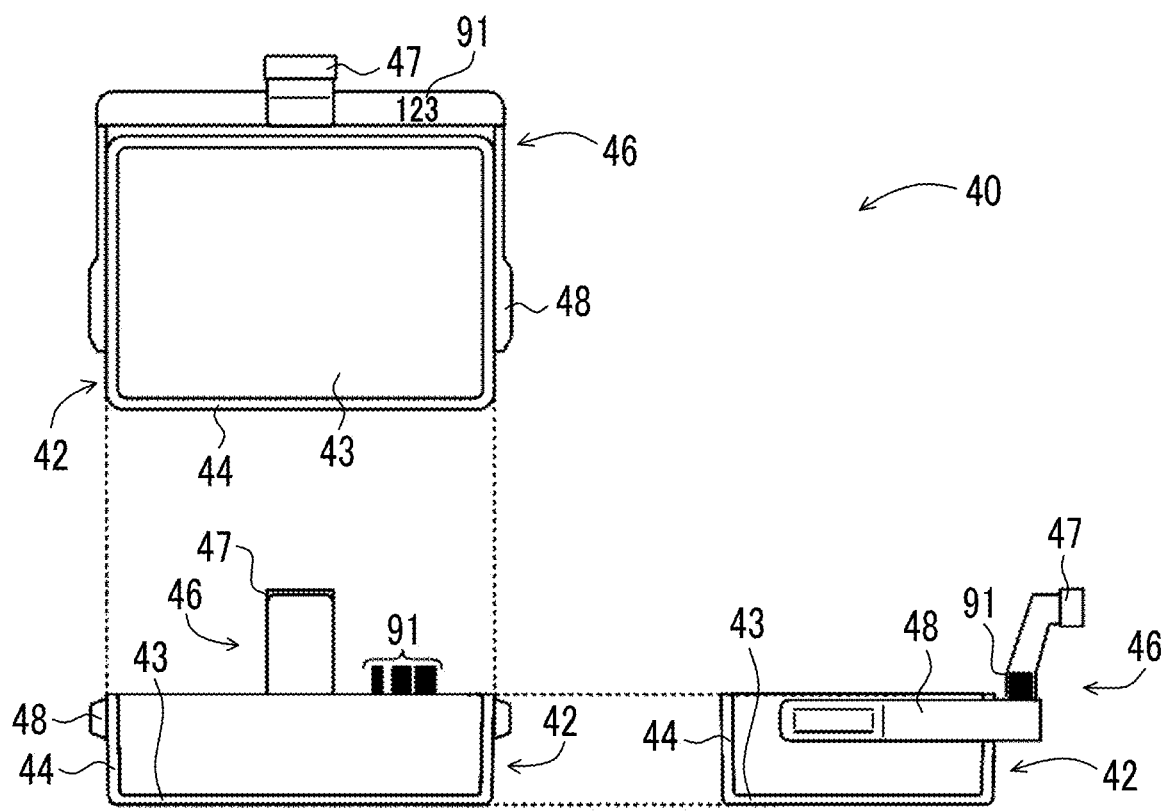
FIG. 10 is a diagram illustrating another example of the identification information given to the compression plate.

In this embodiment, the aspect in which identification information, such as the identification information 90, for identifying the abnormality determination target is read from the visible light image has been described. However, a method for reading the identification information is not limited to this embodiment. For example, as illustrated in FIG. 10, in a case in which identification information 91 that has an uneven shape toward the TOF camera 39 is provided in the abnormality determination target (the compression plate 40 in FIG. 10), the identification information may be read from the distance image captured by the TOF camera 39. The identification information 91 in this embodiment is an example of a mark according to the present disclosure. In the abnormality determination process in this case, instead of the process in Step S103A illustrated in FIG. 9, Step S116 of the abnormality determination process (see FIG. 7) according to the first embodiment may be performed. In addition, in Step S103, the identification information may be read from the distance image.

As described above, the console 12 according to each of the above-described embodiments comprises the CPU 50A as at least one processor and the ROM 50B storing commands that can be executed by the CPU 50A. The CPU 50A acquires the distance image captured by the TOF camera 39, which captures a distance image showing the distance to the imaging target, using the mammography apparatus 10 which is the abnormality determination target as the imaging target. In addition, the CPU 50A acquires the reference distance image 53A as the reference distance information 53 related to the reference value of the distance between the abnormality determination target in the reference state and the TOF camera 39. Further, the CPU 50A determines an abnormality appearing in the outward appearance of the abnormality determination target on the basis of the distance image and the reference distance image 53A.

The above-mentioned configuration makes it possible for the console 12 according to each of the above-described embodiments to determine an abnormality occurring in the outward appearance of the mammography apparatus 10 from the distance image.

Further, according to the console 12 of this embodiment, one distance image can be captured using a plurality of abnormality determination targets as the imaging targets, and abnormality determination can be performed on the plurality of abnormality determination targets on the basis of one distance image. Therefore, according to the console 12 of each of the above-described embodiments, abnormality determination can be performed more easily, as compared to a case in which abnormality determination needs to be performed on each abnormality determination target, for example, a case in which a sensor or the like for abnormality determination is provided for each abnormality determination target.

In addition, in each of the above-described embodiments, for abnormality determination on each abnormality determination target, the aspect in which whether or not an abnormality has occurred, the type of the abnormality that has occurred, and the position where the abnormality has occurred are determined has been described. However, the types of determination related to abnormalities are not limited to the above. For example, the degree of abnormality may be determined. For example, a degree determination threshold value for determining the degree of abnormality may be provided, and it may be determined that the degree of abnormality becomes larger as the threshold value for the above-mentioned difference becomes larger.

Further, in each of the above-described embodiments, the aspect in which the reference distance image 53A is used as the reference distance information 53 has been described. However, the reference distance information 53 is not limited to the reference distance image 53A. For example, the reference distance information 53 may be a reference value based on the design value of the abnormality determination target, the design value and the set value of the radiography system 1, or the like.

Furthermore, in each of the above-described embodiments, the aspect in which the distance image is captured by the TOF method using the TOF camera has been described as an example of the aspect of capturing the distance image. However, the distance image capture device for capturing the distance image is not limited to the TOF camera. For example, the following aspect may be used: a distance image capture device that irradiates an imaging target with infrared light having a pattern and captures a distance image corresponding to reflected light from the imaging target is used, and a structured light method is applied to capture the distance image. Further, for example, a depth-from-defocus (DFD) method that restores the distance on the basis of the degree of blurring of an edge region in the distance image may be applied. In the case of this aspect, for example, an aspect is known which uses a distance image captured by a monocular camera using a color aperture filter.

Further, in each of the above-described embodiments, the aspect has been described in which the TOF camera 39 and the visible light camera 31 are provided on the side close to the compression unit 36 in the radiation emitting unit 37 of the mammography apparatus 10. However, the position where each of the TOF camera 39 and the visible light camera 31 is provided is not limited to this aspect. Each of the TOF camera 39 and the visible light camera 31 may be disposed at any position where it can capture images using, as an imaging region, the entire mammography apparatus 10 or a region including a component. The position is not limited. For example, at least one of the TOF camera 39 or the visible light camera 31 may be provided on the side close to the face guard 38 in the radiation emitting unit 37. In addition, for example, at least one of the TOF camera 39 or the visible light camera 31 may be provided outside the mammography apparatus 10.

Further, in each of the above-described embodiments, the aspect in which the console 12 is an example of the information processing apparatus according to the present disclosure has been described. However, apparatuses other than the console 12 may have the functions of the information processing apparatus according to the present disclosure. In other words, for example, the mammography apparatus 10 or an external apparatus other than the console 12 may have some or all of the functions of the first acquisition unit 60, the second acquisition unit 62, and the determination unit 64.

In each of the above-described embodiments, for example, the following various processors can be used as the hardware structure of processing units performing various processes such as the first acquisition unit 60, the second acquisition unit 62, and the determination unit 64. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the abnormality determination processing program 51 is stored (installed) in the storage unit 52 in advance has been described. However, the present disclosure is not limited thereto. The abnormality determination processing program 51 may be recorded on a recording medium, such as a compact disc read only memory (CD-ROM), a digital versatile disc read only memory (DVD-ROM), or a universal serial bus (USB) memory, and then provided. In addition, the abnormality determination processing program 51 may be downloaded from an external apparatus through the network.

What is claimed is:

1. A radiography system comprising:
    a mammography apparatus comprising a camera configured to capture a distance image indicating a distance between the camera and an abnormality determination target, which is a region on a component of the mammography apparatus, and
    an information processing apparatus comprising at least one processor and a memory that stores commands executable by the processor,
    wherein after the distance image is captured by the camera, the distance image is acquired by the processor and is compared to reference distance information related to a reference value of a distance between the camera and the abnormality determination target in a reference state to determine whether an abnormality is present on the abnormality determination target.

2. The radiography system according to claim 1,
    wherein the processor determines that the abnormality has occurred in a case in which an absolute value of a difference between a distance to the abnormality determination target indicated by the distance image and the reference value is greater than an abnormality determination threshold value.

3. The radiography system according to claim 2,
    wherein, in a case in which it is determined that the abnormality has occurred, the processor determines that, as the absolute value of the difference becomes larger, a degree of the abnormality becomes larger.

4. The radiography system according to claim 2,
    wherein the processor specifies an abnormal region that is greater than the abnormality determination threshold value in the distance image and determines that deflection has occurred as the abnormality in a case in which a width of the specified abnormal region is equal to or greater than a type determination threshold value.

5. The radiography system apparatus according to claim 2,
wherein the processor specifies an abnormal region that is greater than the abnormality determination threshold value in the distance image and determines that a scratch or a crack has occurred as the abnormality in a case in which a width of the specified abnormal region is less than a type determination threshold value.

6. The radiography system according to claim 2,
wherein the abnormality determination target is at least one of a plurality of components in the mammography apparatus, and
the abnormality determination threshold value is determined for each of the plurality of components.

7. The radiography system according to claim 6,
wherein the plurality of components are provided with marks including portions having different distances from the distance image capture device, and
the processor determines which of the plurality of components is the abnormality determination target from an image of the mark in the distance image.

8. The radiography system according to claim 1,
wherein the abnormality determination target is at least one of a plurality of components in the mammography apparatus, and
the reference distance information is determined for each of the plurality of components.

9. The radiography system according to claim 1,
wherein the processor acquires a visible light image of the abnormality determination target captured by a visible light image capture device that captures the visible light image, acquires a reference visible light image obtained by capturing an image of the abnormality determination target in the reference state, and performs determination on the abnormality appearing in the outward appearance of the mammography apparatus on the basis of the distance image, the reference distance information, the visible light image, and the reference visible light image.

10. The radiography system according to claim 9,
wherein, in a case in which it is determined that no abnormality has occurred in the outward appearance of the mammography apparatus on the basis of the distance image and the reference distance information and that an abnormality has occurred in the outward appearance of the mammography apparatus on the basis of the visible light image and the reference visible light image, the processor determines that a stain has occurred as the abnormality.

11. The radiography system according to claim 1,
wherein the reference distance information is a reference distance image indicating a distance between the distance image capture device and the abnormality determination target disposed at a reference position.

12. The radiography system according to claim 11,
wherein, in a case in which the abnormality determination target is not disposed at the reference position, after moving the abnormality determination target to the reference position, the processor directs the distance image capture device to capture the distance image, and acquires the distance image captured by the distance image capture device.

13. The radiography system according to claim 1,
wherein the abnormality is at least one of a scratch, a crack, deflection, or a stain.

14. The radiography system according to claim 1,
wherein the abnormality determination target is a compression member that is attached to the mammography apparatus.

15. The radiography system according to claim 1,
wherein the abnormality determination target is an imaging table of the mammography apparatus.

16. The radiography system according to claim 1,
wherein the abnormality determination target is a biopsy-related member that is attached to the mammography apparatus.

17. The radiography system according to claim 1,
wherein the distance image capture device captures the distance image using a time-of-flight (TOF) method.

18. An information processing method executable by a computer, the method comprising:
acquiring a distance image that indicates a distance between a camera and an abnormality determination target, the camera being disposed on a mammography apparatus and the abnormality determination target being a region on a component of the mammography apparatus;
acquiring reference distance information related to a reference value of a distance between the camera and the abnormality determination target in a reference state; and
determining whether an abnormality is present on the abnormality determination target by comparing the distance image and the reference distance information.

19. A non-transitory computer-readable storage medium storing an information processing program that causes a computer to perform a process comprising:
acquiring a distance image that indicates a distance between a camera and an abnormality determination target, the camera being disposed on a mammography apparatus and the abnormality determination target being a region on a component of the mammography apparatus;
acquiring reference distance information related to a reference value of a distance between the camera and the abnormality determination target in a reference state; and
determining whether an abnormality is present on the abnormality determination target by comparing the distance image and the reference distance information.

* * * * *